(12) United States Patent
Kinoshita et al.

(10) Patent No.: US 9,856,196 B2
(45) Date of Patent: Jan. 2, 2018

(54) AGENT FOR REDUCTION OF SENSORY IRRITATION

(71) Applicant: Kao Corporation, Chuo-ku, Tokyo (JP)

(72) Inventors: Kazuki Kinoshita, Tochigi (JP); Tomohiro Shirai, Utsunomiya (JP); Kentaro Kumihashi, Utsunomiya (JP); Hirohisa Fujihara, Cincinnati, OH (US); Nanae Mugita, Tokyo (JP)

(73) Assignee: Kao Corporation, Tokyo (JP)

( * ) Notice: Subject to any disclaimer, the term of this patent is extended or adjusted under 35 U.S.C. 154(b) by 60 days.

(21) Appl. No.: 14/361,038

(22) PCT Filed: Jan. 4, 2013

(86) PCT No.: PCT/JP2013/050347
§ 371 (c)(1),
(2) Date: May 28, 2014

(87) PCT Pub. No.: WO2013/103155
PCT Pub. Date: Jul. 11, 2013

(65) Prior Publication Data
US 2014/0323586 A1    Oct. 30, 2014

(30) Foreign Application Priority Data
Jan. 5, 2012    (JP) ................. 2012-000775

(51) Int. Cl.
*C07C 33/30* (2006.01)
*A61K 31/045* (2006.01)
*C07C 31/125* (2006.01)

(52) U.S. Cl.
CPC ............ *C07C 33/30* (2013.01); *A61K 31/045* (2013.01); *C07C 31/125* (2013.01)

(58) Field of Classification Search
CPC ...... A61K 31/045; C07C 31/125; C07C 33/30
See application file for complete search history.

(56) References Cited

U.S. PATENT DOCUMENTS

| 4,458,699 | A | * | 7/1984 | Schreck ............... A24B 15/301 131/276 |
| 4,610,812 | A | | 9/1986 | Hall |
| 2005/0009997 | A1 | | 1/2005 | Spino et al. |
| 2010/0280108 | A1 | | 11/2010 | Rodriguez et al. |
| 2011/0034549 | A1 | | 2/2011 | Rodriguez et al. |

FOREIGN PATENT DOCUMENTS

| CA | 2413713 A1 | 6/2004 |
| DE | 31 03 268 A1 | 8/1982 |
| DE | 19541967 A1 | 5/1997 |
| JP | 2008-079528 A | 4/2008 |
| JP | 2009-082053 A | 4/2009 |
| JP | 2009-225733 A | 10/2009 |
| WO | WO 2009/080769 A1 | 7/2009 |

OTHER PUBLICATIONS

Talavera et al., "Nicotine activates the chemosensory cation channel TRPA1," Nature Neuroscience, 2009; 12(10): pp. 1293-1300.*
International Search Report (ISR) for PCT/JP2013/050347; I.A. fd: Jan. 4, 2013, dated Mar. 25, 2013 from the European Patent Office, Rijswijk, Netherlands.
International Preliminary Report on Patentability (IPRP), Chapter I of the Patent Cooperation Treaty, including the Written Opinion for PCT/JP2013/050347; I.A. fd: Jan. 4, 2013, dated Jul. 8, 2014, by the International Bureau of WIPO, Geneva, Switzerland.
Story, GM et al., "ANKTM1, a TRP-like channel expressed in nociceptive neurons, is activated by cold temperatures," Cell, Mar. 2003; 112(6): 819-829, Cell Press, Cambridge, MA.
Kwan, Ky et al., "TRPA1 contributes to cold, mechanical, and chemical nociception but is not essential for hair-cell transduction," Neuron, Apr. 2006; 50(2): 277-289, Cell Press, Cambridge, MA.
Tominaga, M, "New development 3 of sense-based reactions of drugs—Molecular mechanism of the temperature reception—TRP channel temperature sensor," Nihon Yakurigaku Zasshi (Japanese reactions of drugs magazine; Folia Pharmacol. Jpn), Oct. 2004; 124(4): 219-227, Nippon Yakuri Gakkai, Tokyo, Japan.
Eid, SR et al., "HC-030031, a TRPA1 selective antagonist, attenuates inflammatory- and neuropathy-induced mechanical hypersensitivity," Mol Pain, Jan. 2008; 4:48 (10 pages) doi:10.1186/1744-8069-4-48, BioMed Central, London, England.
Aithie, GCM et al., "ilsoprene epoxide as a hemiterpenoid synthon," Tetrahedron Letters No. 49, 4419-4420 (1975); Pergamon Press, Oxford, England.

(Continued)

*Primary Examiner* — Sreeni Padmanabhan
*Assistant Examiner* — Jody Karol
(74) *Attorney, Agent, or Firm* — Sterne, Kessler, Goldstein & Fox P.L.L.C.

(57) ABSTRACT

Provision of a TRPA1 activity inhibitor capable of reducing sensory irritation to skin or mucous membrane and an agent for reduction of sensory irritation for skin or mucous membrane. A TRPA1 inhibitor and an agent for reduction of sensory irritation for skin or mucous membrane comprising as an active ingredient a compound represented by the following formula (1) wherein $R^1$ and $R^3$ each independently represent a hydrogen atom or an alkyl group having 1 to 3 carbon atoms, $R^2$ represents an alkyl group having 1 to 6 carbon atoms, $R^4$ represents a hydrogen atom, a methyl group or an ethyl group, and a double line composed of a dotted line and a solid line represents a single bond or a double bond.

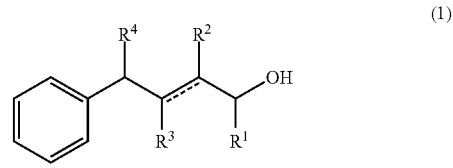

(1)

11 Claims, 3 Drawing Sheets

(56) References Cited

OTHER PUBLICATIONS

Stymiest, JL et al., Lithiated carbamates: chiral carbenoids for iterative homologation of boranes and boronic esters, Angew Chem Int Ed Engl, Jan. 2007; 46(39): 7491-7494, Wiley-VCH, Weinheim, Germany.

Abate, A et al., "Chirality and fragrance chemistry: stereoisomers of the commercial chiral odorants Muguesia and Pamplefleur," J Org Chem, Feb. 2005; 70(4): 1281-1290, Am. Chem. Soc., Columbus, OH.

Komatsu, T et al., "Primary alcohols activate human TRPA1 channel in a carbon chain length-dependent manner," Pflugers Arch, Apr. 2012; 463(4): 549-559, Springer, NY.

Benzyl Alcohol CASRN:100-51-6, author unknown, Toxnet—Toxicology Data Network, National Library of Medicine HSDB Database, last revision: Feb. 18, 2015, downloaded Jul. 18, 2017 from https://toxnet.nlm.nih.gov/cgi-bin/sis/search/a?dbs+hsdb:@term+@DOCNO+46, Division of Specialized Information Services, US Dept. of Health and Human Services, Bethesda, MD.

* cited by examiner

[Fig.1]
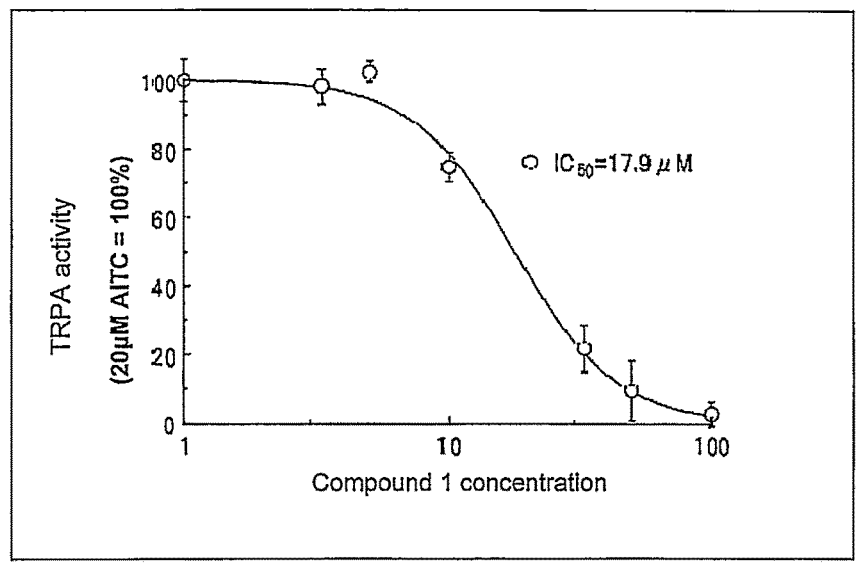
[Fig.2]
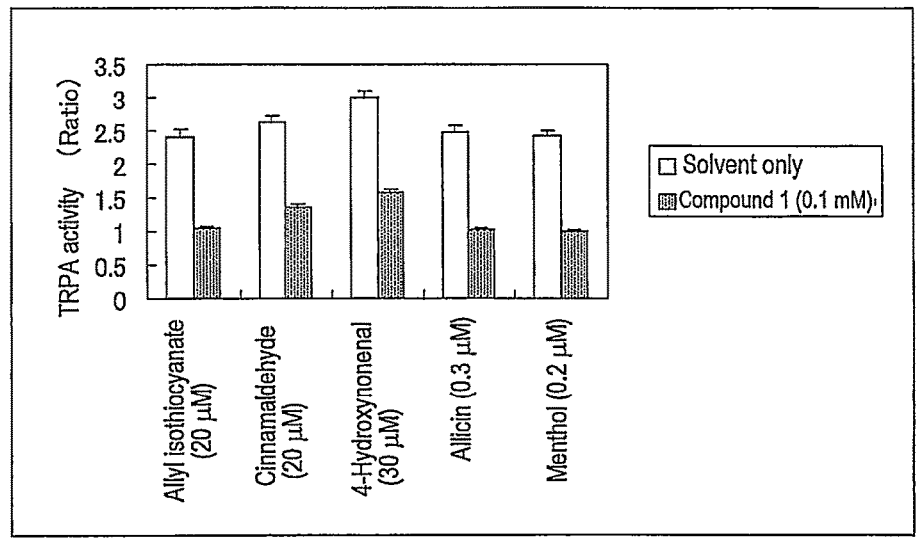

[Fig.3]
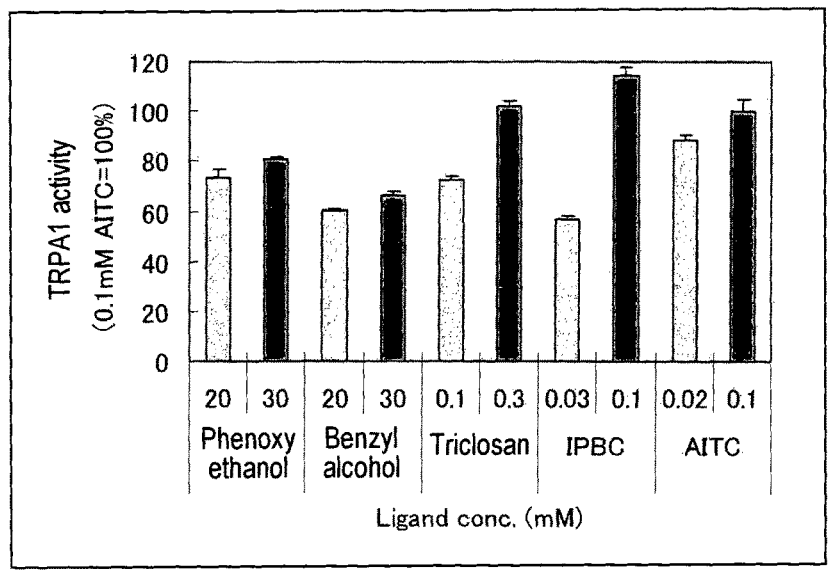
[Fig.4]
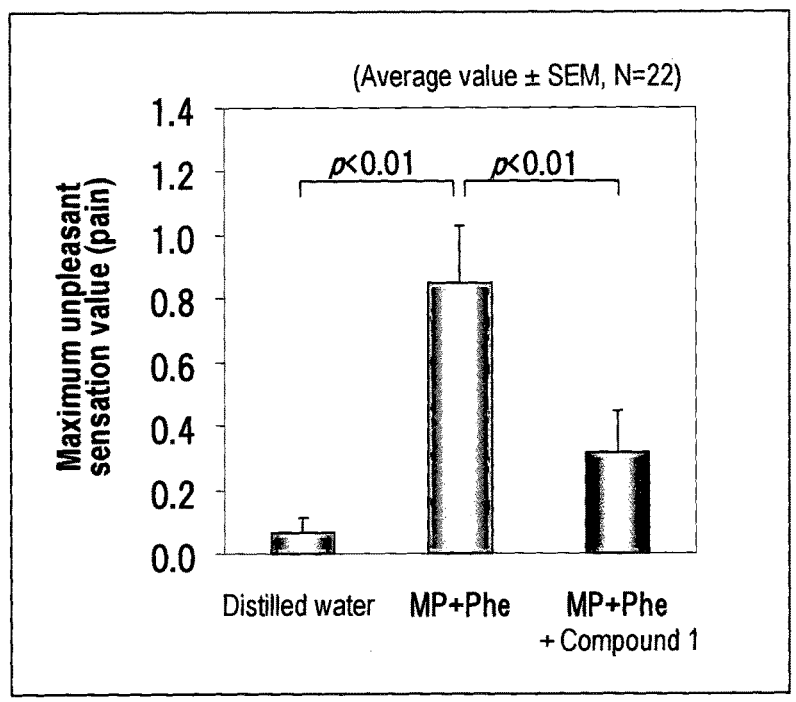

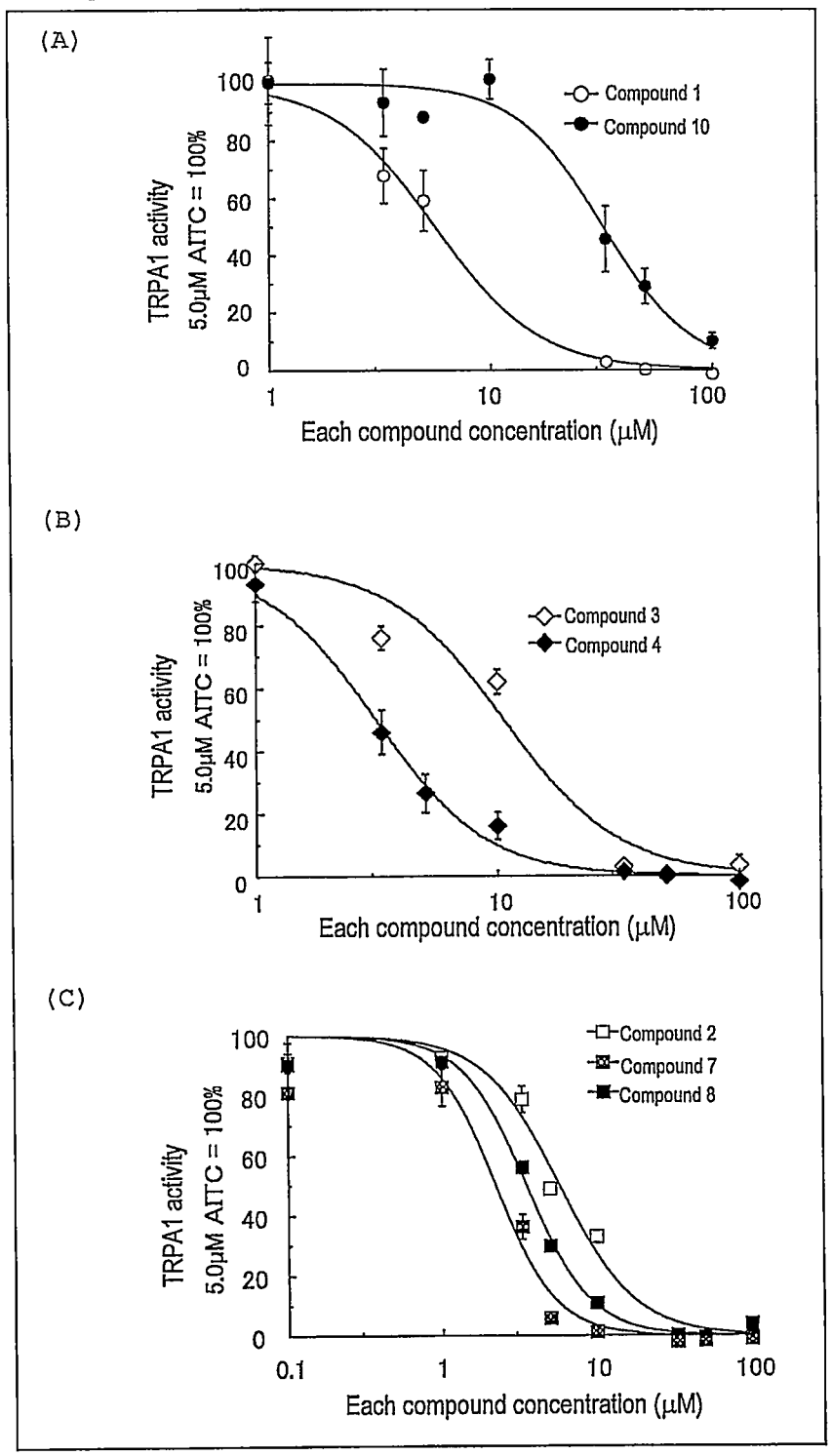
[Fig.5]

AGENT FOR REDUCTION OF SENSORY IRRITATION

FIELD OF THE INVENTION

The present invention relates to a TRPA1 inhibitor and an agent for reduction of sensory irritation.

BACKGROUND OF THE INVENTION

Sensation is produced when stimulation received from outside is converted to an electrical signal and transmitted to the brain through nerve cells. To convert external stimulation to an electrical signal, the existence of a receptor to perceive the external stimulation is essential.

TRPA1 is a non-selective cation channel belonging to a superfamily of transient receptor potential (TRP) ion channel and was found as a cold-temperature receptor (17° C.) in nociceptive neurons (Non Patent Document 1). After that, it is reported that TRPA1 is a chemoreceptor which responds to mustard oil, allyl isothiocyanate (AITC) contained therein, cinnamon, garlic, methyl salicylate, eugenol and the like, and is a pain receptor which responds to a cold temperature, mechanical and chemical stimulation (Non Patent Documents 2 and 3).

Further, it is recently reported that parabens and alkali agents respond to TRPA1 and substances which suppress irritation caused by parabens and alkali agents can be screened using transformed cells by TRPA1 gene (Patent Documents 1 and 2).

Thus, TRPA1 is a nociceptor of skin and mucous membrane and activated by various stimulation, and therefore inhibition of TRPA1 activity is considered to be effective to reduce the pain caused by various stimulation and so far agents for reduction of sensory irritation have been searched and evaluated by contacting a test agent and AITC with TRPA1-expressing cells and measuring the changes of intracellular calcium ion concentration induced by AITC through TRPA1 (Non Patent Document 4).

CITATION LIST

Patent Document

[Patent Document 1] JP-A-2008-79528
[Patent Document 2] JP-A-2009-82053

Non Patent Document

[Non Patent Document 1] Story et al. 2003, Cell 112, 819-829
[Non Patent Document 2] Kwan et al. 2006, Neuron 50, 277-289
[Non Patent Literature 3] Folia Pharmacologica Japonica, Vol. 124, pp. 219-227, 2004, published by The Japanese Pharmacological Society
[Non Patent Document 4] Molecular Pain 2008, 4: 48

SUMMARY OF THE INVENTION

The present invention relates to the following 1) to 8).

1) A TRPA1 inhibitor comprising as an active ingredient a compound represented by the following formula (1).

2) An agent for reduction of sensory irritation for skin or mucous membrane comprising as an active ingredient a compound represented by the following formula (1).

3) Use of a compound represented by the following formula (1) for the production of a TRPA1 inhibitor.

4) Use of a compound represented by the following formula (1) for the production of an agent for reduction of sensory irritation for skin or mucous membrane.

5) A compound represented by the following formula (1) for use in inhibition of TRPA1 activity.

6) A compound represented by the following formula (1) for use in reduction of sensory irritation for skin or mucous membrane.

7) A method for inhibiting TRPA1 activity comprising using a compound represented by the following formula (1).

8) A method for reducing sensory irritation for skin or mucous membrane comprising using a compound represented by the following formula (1).

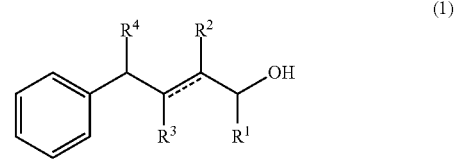

wherein $R^1$ and $R^3$ each independently represent a hydrogen atom or an alkyl group having 1 to 3 carbon atoms; $R^2$ represents an alkyl group having 1 to 6 carbon atoms, $R^4$ represents a hydrogen atom, a methyl group or an ethyl group, and a double line composed of a dotted line and a solid line represents a single bond or a double bond.

BRIEF DESCRIPTION OF DRAWINGS

FIG. 1 is a graph showing the inhibitory effect of Compound 1 on TRPA1 activation caused by AITC (dose dependency).

FIG. 2 is a graph showing the effect of Compound 1 on TRPA1 activation caused by various TRPA1 stimulants.

FIG. 3 is a graph showing TRPA1 activation caused by antiseptics and antiseptic aids.

FIG. 4 is a graph showing the effect of Compound 1 on sensory irritation caused by antiseptics.

FIGS. 5(A), 5(B) and 5(C) are graphs showing the inhibitory effect (dose dependency) of the compounds of the present invention on TRPA1 activation:
(A): Compound 10, Compound 1, (B): Compound 3, Compound 4,
(C): Compound 7, Compound 8, and Compound 2.

DETAILED DESCRIPTION OF THE INVENTION

The present invention relates to the provision of a TRPA1 inhibitor capable of reducing the sensory irritation for skin or mucous membrane and an agent for reduction of sensory irritation for skin or mucous membrane.

The present inventors evaluated materials which inhibit the activity of TRPA1 and found that the compound represented by the above formula (1) inhibits the activity of TRPA1 and is effective to reduce sensory irritation for skin or mucosa membrane caused by a causative substance of sensory irritation.

The TRPA1 inhibitor and the agent for reduction of sensory irritation for skin or mucous membrane of the present invention have potential to effectively inhibit the activation of TRPA1. Accordingly, when the TRPA1 inhibitor or the agent for reduction of sensory irritation for skin or mucous membrane is used with various compositions containing a causative substance of sensory irritation such as an antiseptic, an antiseptic aid, ammonia or the like, the sensory irritation and pain caused by such a causative substance can be alleviated.

In the formula (1) of the present invention, the alkyl group having 1 to 3 carbon atoms represented by $R^1$ and $R^3$ may be either linear or branched and specific examples include a methyl group, an ethyl group, an n-propyl group and an isopropyl group, among which a methyl group is preferable.

It is preferable that $R^1$ and $R^3$ are both hydrogen atoms or either one of them is an alkyl group having 1 to 3 carbon atoms (preferably a methyl group).

The alkyl group having 1 to 6 carbon atoms represented by $R^2$ may be either linear or branched and examples thereof include a methyl group, an ethyl group, an n-propyl group, an isopropyl group, an n-butyl group, a t-butyl group, an n-pentyl group, an n-hexyl group and the like, among which an alkyl group having 1 to 3 carbon atoms is preferable, with a methyl group and an ethyl group being more preferable.

Preferred embodiment of the compound represented by the formula (1) of the present invention includes a case wherein $R^1$ is a hydrogen atom or a methyl group, $R^2$ is a methyl group or an ethyl group, $R^3$ is a hydrogen atom and $R^4$ is a methyl group or an ethyl group.

The compound wherein $R^1$ and $R^3$ are both hydrogen atoms, $R^2$ and $R^4$ are both methyl groups and a double line composed of a dotted line and a solid line represents a single bond, namely, 2-methyl-4-phenyl-1-pentanol (Compound 1) is a substance used in skin care products, softeners or the like as a long-lasting fragrance and commercially available under the name of "Pamplefleur".

Further, in the compound represented by the formula (1) of the present invention wherein the double line composed of a dotted line and a solid line represents a double bond, the cis isomer (Z isomer) and the trans isomer (E isomer) exist. Also, depending on the type and combination of substituents, isomers such as optical isomers including d-isomer, l-isomer and the like and rotational isomers, may exist. In the present invention, any of the mixtures and isolates of these isomers are encompassed.

The compound represented by the formula (1) of the present invention can be chemically synthesized in accordance with a known method (e.g., J. Org. Chem. 2005, 70, 1281-1290). For example, the compound can be synthesized, as shown in the following reaction formula, by condensing a carbonyl compound represented by A and triester of phosphonocarboxylic acid or the like in the presence of a base to form an α,β unsaturated ester B, subjecting the ester B to a reduction reaction using LiAlH$_4$ or the like to form an alcohol C, further hydrogenating the alcohol C to form a saturated alcohol D, furthermore subjecting the alcohol D to an oxidation reaction using TEMPO and iodobenzene diacetate or the like to form an aldehyde E and incorporating an alkyl group using an alkylating agent such as a Grignard reagent to form Compound F.

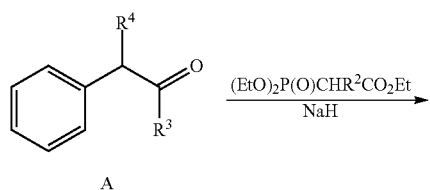

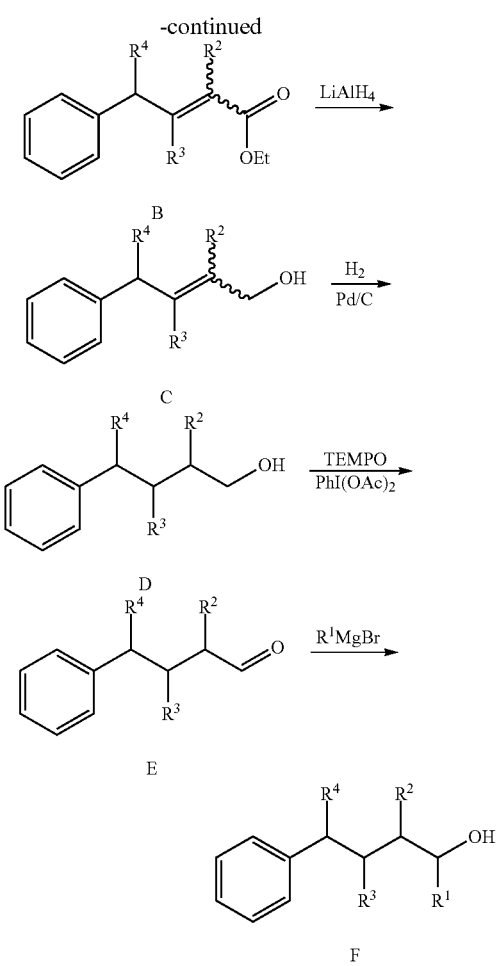

wherein $R^1$ to $R^4$ are as defined above.

Further, a commercially available "pamplefleur" (IFF Inc.) or the like can also be used as the 2-methyl-4-phenyl-1-pentanol.

Examples of the more preferred compound of the compound represented by the formula (1) include those listed in Table 1 to be described later, among which 2-methyl-4-phenyl-1-pentanol (Compound 1), (E)-2-ethyl-4-phenyl-2-penten-1-ol (Compound 2), (Z)-2-ethyl-4-phenyl-2-penten-1-ol (Compound 3), 2-ethyl-4-phenyl-1-pentanol (Compound 4), (E)-2-ethyl-4-phenyl-2-hexen-1-ol (Compound 7), (Z)-2-ethyl-4-phenyl-2-hexen-1-ol (Compound 8) and (E)-2-methyl-4-phenyl-2-penten-1-ol (Compound 10) are preferable in light of the inhibitory effect on TRPA1 activation.

The compound represented by the formula (1) of the present invention, as demonstrated in Examples to be described later, has the inhibitory effect on TRPA1 activation by inhibiting the inflow of an intracellular cation amount caused by stimulants when allowed, together with various TRPA1 stimulants, to contact a TRPA1-transduced cell (TRPA1 expression cell) (Examples 1 to 4, 7 and 8). Also, when the compound represented by the formula (1) of the present invention is applied to skin together with an antiseptic which activates TRPA1, the compound exhibits the effect to alleviate sensory irritation property caused by the antiseptic and irritating odor (Examples 5 and 6).

Thus, the compound represented by the formula (1) of the present invention may be a TRPA1 inhibitor and an agent for reduction of sensory irritation for skin or mucous membrane effective to alleviate sensory irritation and pain to skin or mucous membrane induced through TRPA1.

The "inhibition of TRPA1 activity" used herein refers to inhibition of TRPA1 activity, which is a receptor; specifically, the inhibition or blockage of the activation expressed when a TRPA1 stimulant (agonist) bonds to TRPA1, for example, the regulatory capacity of ion flux (e.g., the transport capacity of cations such as calcium ion, sodium ion or the like from outside to inside of a cell), the regulatory capacity of membrane potential (e.g., current generating capacity).

Examples of the TRPA1 stimulant herein include AITC, ammonia, bradykinin, cinnamaldehyde, 4-hydroxynonenal, allicin, acrolein, menthol, methyl salicylate, eugenol, parabens, phenoxyethanol, iodopropynyl butylcarbamate (IPBC), triclosan, benzyl alcohol and the like.

The inhibitory effect on TRPA1 activation of the compound represented by the formula (1) of the present invention can be evaluated, for example, using a TRPA1 expression cell, by comparing the difference between the calcium ion concentration in the TRPA1-expressing cell which is contacted with a TRPA1 stimulant (e.g., AITC) in the presence of the compound represented by the formula (1) and the calcium ion concentration in the TRPA1-expressing cell which is contacted a TRPA1 stimulant in the absence of the compound represented by the formula (1).

Further, the "reducing sensory irritation of skin or mucous membrane" means to inhibit or alleviate the sensory irritation and pain induced through TRPA1 activation; more specifically, the term means the inhibition or alleviation of the sensory irritation caused by chemical substances, which are the TRPA1 stimulants described above. Preferred TRPA1 stimulants herein are chemical substances which may cause sensory irritation to skin or mucous membrane (referred to as "causative substance of sensory irritation"), and examples include antiseptics such as parabens, phenoxyethanol, iodopropynyl butylcarbamate (IPBC) and triclosan, antiseptic aids such as benzyl alcohol, ammonia, acrolein, menthol, methyl salicylate, eugenol and the like.

The "mucous membrane" used herein includes the oral cavity, throat, nasal cavity, ear cavity, conjunctival sac and the like.

The effect that reduces sensory irritation may be measured by the sensory evaluation as shown in Examples to be described later or may be evaluated based on the changes of intracellular calcium ion concentration using the above-described TRPA1-expressing cell.

The TRPA1 inhibitor and the agent for reduction of sensory irritation for skin or mucous membrane of the present invention may be added to a composition containing a causative substance of sensory irritation described above (cosmetics, quasi drugs, pharmaceutical products, daily supplies or the like which include skin cleansers, head and hair cleansers, make-up agents, bath agents, perm solutions, hair dyes, soaps, detergents, laundry detergents, toothpastes and the like) or may be combined with the composition. For example, the TRPA1 inhibitor and the agent for reduction of sensory irritation for skin or mucous membrane of the present invention may be prepared separately from a composition containing a causative substance of sensory irritation and combined simultaneously or successively therewith. Thus, the sensory irritation caused by such a causative substance of sensory irritation can be reduced.

The TRPA1 inhibitor and the agent for reduction of sensory irritation for skin or mucous membrane may be the compound represented by the formula (1) of the present invention which is used singly, or may be a composition combined with an additive, an excipient or the like used in various preparations such as pharmaceutical products, cosmetics, quasi drugs and daily supplies, including oils, colorants, flavors, antiseptics, chelating agents, pigments, antioxidants, vitamins, minerals, sweeteners, seasonings, preservatives, binders, extenders, disintegrators, surfactants, lubricants, dispersants, buffers, coating agents, carriers, diluents or the like. Further, the form thereof is not limited and the inhibitor and the agent can be prepared in any form, for example, solutions, emulsions, suspensions, gels, solids, powders, particulates and aerosols.

When the TRPA1 inhibitor and the agent for reduction of sensory irritation for skin or mucous membrane of the present invention are used with a composition containing a causative substance of sensory irritation, the amount of the TRPA1 inhibitor and the agent for reduction of sensory irritation for skin or mucous membrane to be used is not limited insofar as the effect that reduces sensory irritation is achieved. But, the amount of the compound represented by the formula (1) of the present invention may be preferably 0.01 parts by mass or more, more preferably 0.1 parts by mass or more, and preferably 10 parts by mass or less, more preferably 1 part by mass or less per part by mass of a causative substance of sensory irritation. For example, the amount to be used may be preferably 0.01 to 10 parts by mass, more preferably 0.1 to 1 part by mass, per part by mass of a causative substance of sensory irritation.

Regarding the above embodiments, the present invention further discloses the following embodiments.

<1> A TRPA1 inhibitor comprising as an active ingredient a compound represented by the following formula (1).

<2> An agent for reduction of sensory irritation for skin or mucous membrane comprising as an active ingredient a compound represented by the following formula (1).

<3> Use of a compound represented by the following formula (1) for the production of a TRPA1 inhibitor.

<4> Use of a compound represented by the following formula (1) for the production of an agent for reduction of sensory irritation for skin or mucous membrane.

<5> A compound represented by the following formula (1) for use in inhibition of TRPA1 activity.

<6> A compound represented by the following formula (1) for use in reduction of sensory irritation of skin or mucous membrane.

<7> A method for inhibiting the TRPA1 activity comprising using a compound represented by the following formula (1).

<8> A method for reducing sensory irritation to skin or mucous membrane comprising using a compound represented by the following formula (1).

<9> In the above <2>, <4>, <6> or <8>, the reduction of sensory irritation is reduction of the sensory irritation to skin or mucous membrane caused by a causative substance of sensory irritation.

<10> In the above <9>, the causative substance of sensory irritation is an antiseptic, an antiseptic aid or ammonia.

<11> In the above <5>, <6>, <7> or <8>, the compound represented by the following formula (1) is added to a composition containing a causative substance of sensory irritation, or combined with the composition.

<12> In the above <11>, the compound represented by the following formula (1) is used in an amount of preferably 0.01 parts by mass or more, more preferably 0.1 parts by mass or more, and preferably 10 parts by mass or less, more preferably 1 part by mass or less, per part by mass of a causative substance of sensory irritation.

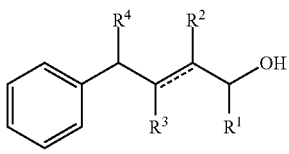
(1)

In the formula (1), $R^1$ and $R^3$ each independently represent a hydrogen atom or an alkyl group having 1 to 3 carbon atoms, $R^2$ represents an alkyl group having 1 to 6 carbon atoms, $R^4$ represents a hydrogen atom, a methyl group or an ethyl group, and a double line composed of a dotted line and a solid line represents a single bond or a double bond.

EXAMPLES

Production Example

Hereinbelow, Production Examples of the compounds of the present invention (Compounds 1 to 12) shown in Table 1 and the Comparative Compounds are described. For Compound 1 (2-methyl-4-phenyl-1-pentanol), a commercially available "pamplefleur" (IFF Inc.) was purchased.

$^1$H-NMR spectrum was measured by a Bruker Avance-600 using $CHCl_3$ (7.24) as the internal standard substance, and $^{13}C$ NMR spectrum was measured by a Bruker Avance-600 using $CHCl_3$ (77.0) as the internal standard substance.

TABLE 1

| Compound | Name | Structure |
|---|---|---|
| Compound 1 | 2-methyl-4-phenyl-1-pentanol | |
| Compound 2 | (E)-2-ethyl-4-phenyl-2-penten-1-ol | |
| Compound 3 | (Z)-2-ethyl-4-phenyl-2-penten-1-ol | |
| Compound 4 | 2-ethyl-4-phenyl-1-pentanol | |
| Compound 5 | 2-methyl-4-phenyl-2-hexen-1-ol | |
| Compound 6 | 2-methyl-4-phenyl-1-hexanol | 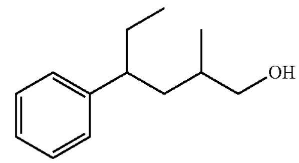 |
| Compound 7 | (E)-2-ethyl-4-phenyl-2-hexen-1-ol | 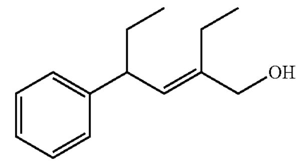 |
| Compound 8 | (Z)-2-ethyl-4-phenyl-2-hexen-1-ol | 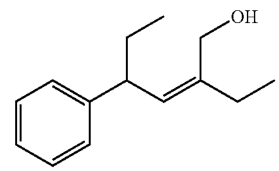 |
| Compound 9 | 2,3-dimethyl-4-phenyl-1-butanol | 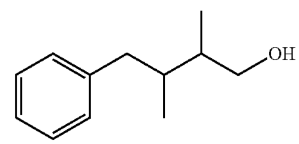 |
| Compound 10 | (E)-2-methyl-4-phenyl-2-penten-1-ol | 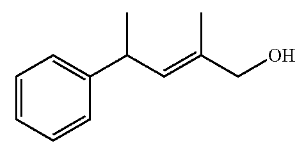 |
| Compound 11 | 2-methyl-4-phenyl-1-butanol | 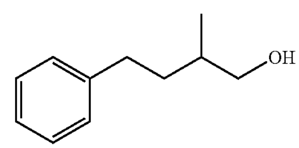 |
| Compound 12 | 3-methyl-5-phenyl-2-hexanol | 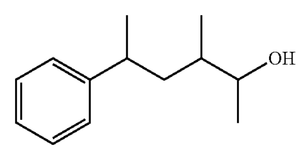 |

Production Example 1 Synthesis of Compounds 2 to 4

(1) Sodium hydride (purity 55%, 195 mg) was suspended in tetrahydrofuran (15 mL), triethyl 2-phosphonobutyrate (1.33 mL) was added thereto and the solution was stirred for 30 minutes at room temperature under nitrogen atmosphere. A solution of 2-phenylpropionaldehyde (a) (300 mg) dissolved in tetrahydrofuran (5 mL) was added to the reaction solution and further stirred for 15 hours. An aqueous solution of saturated ammonium chloride and hexane were added to the reaction solution and the hexane layer was dried under reduced pressure and subsequently purified by silica gel chromatography, thereby obtaining (E)-α,β unsaturated ester (b) (35.9 mg) and (Z)-α,β unsaturated ester (c) (396.4 mg).

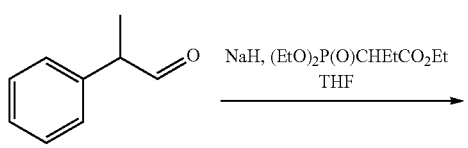

a

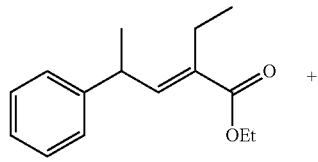

b

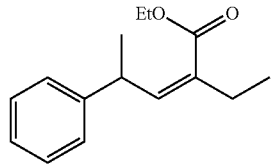

c (2) LiAlH$_4$ (9.6 mg) was suspended in tetrahydrofuran (1 mL), a solution of the (E)-α,β unsaturated ester (b) (23.5 mg) obtained in (1) dissolved in tetrahydrofuran (0.5 mL) was added thereto and stirred at 0° C. for 30 minutes. Water (20 LμL), a 15% sodium hydroxide aqueous solution (20 μL) and water (60 μL) were added in this order to the reaction solution and stirred for a day, followed by filtering the insoluble matters. The filtrate was dried under reduced pressure and purified by silica gel chromatography, thereby obtaining (E)-2-ethyl-4-phenyl-2-penten-1-ol (Compound 2) (14.0 mg).

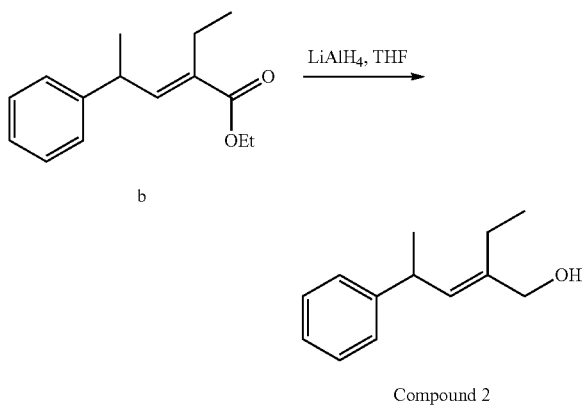

Compound 2

The NMR spectrum of Compound 2 is shown below.
$^1$HNMR (600 MHz, CDCl$_3$) δ 7.30-7.26 (m, 2H), 7.25-7.22 (m, 2H), 7.19-7.15 (m, 1H), 5.52 (d, J=9.8 Hz, 1H), 4.04 (s, 2H), 3.72 (dq, J=9.8, 7.0 Hz, 1H), 2.24-2.13 (m, 2H), 1.34 (d, J=7.0 Hz, 3H), 1.00 (t, J=7.5 Hz, 3H);
$^{13}$CNMR (150 MHz, CDCl$_3$) δ 146.7, 139.5, 131.2, 128.6, 127.0, 126.1, 66.7, 37.6, 22.6, 21.4, 13.5.

(3) LiAlH$_4$ (151 mg) was suspended in tetrahydrofuran (9 mL), a solution of the (Z)-α,β unsaturated ester (c) (371 mg) obtained in (1) dissolved in tetrahydrofuran (6 mL) was added thereto and stirred at 0° C. for 30 minutes. Water (200 μL), a 15% sodium hydroxide aqueous solution (200 μL) and water (600 μL) were added in this order to the reaction solution and stirred for a day, followed by filtering the insoluble matters. The filtrate was dried under reduced pressure and purified by silica gel chromatography, thereby obtaining (Z)-2-ethyl-4-phenyl-2-penten-1-ol (Compound 3) (258 mg).

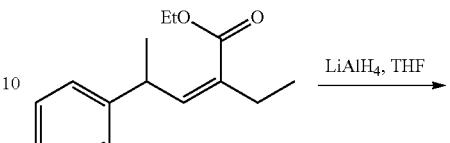

c

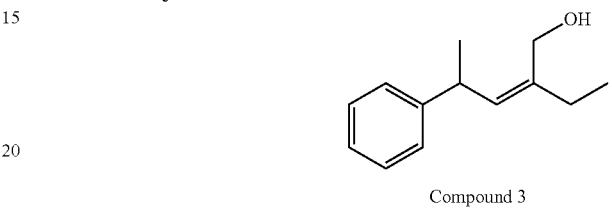

Compound 3

The NMR spectrum of Compound 3 is shown below.
$^1$HNMR (600 MHz, CDCl$_3$) δ 7.30-7.26 (m, 2H), 7.23-7.21 (m, 2H), 7.19-7.15 (m, 1H), 5.44 (d, J=9.5 Hz, 1H), 4.20 (d, J=11.9 Hz, 1H), 4.17 (d, J=11.9 Hz, 1H), 3.79 (dq, J=9.5, 6.9 Hz, 1H), 2.14 (q, J=7.4 Hz, 2H), 1.33 (d, J=6.9 Hz, 3H), 1.03 (t, J=7.4 Hz, 3H);
$^{13}$CNMR (150 MHz, CDCl$_3$) δ 146.8, 139.0, 132.5, 128.5, 126.8, 126.0, 60.7, 37.5, 27.8, 23.0, 12.7.

Compound 3 (80.1 mg) obtained in (4) was dissolved in ethyl acetate (8 mL), Pd/C (10%, 40.0 mg) was added under nitrogen atmosphere, subsequently the system was replaced with hydrogen gas and the solution was stirred at room temperature for 3 hours. The reaction solution was celite-filtered, the filtrate was dried under reduced pressure and purified by silica gel chromatography, thereby obtaining 2-ethyl-4-phenyl-1-pentanol (dr=65:35, Compound 4) (53.8 mg).

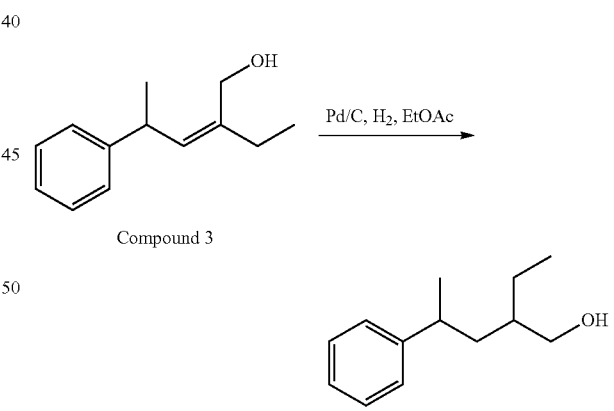

Compound 4

The NMR spectrum of Compound 4 is shown below.
$^1$HNMR (600 MHz, CDCl$_3$) δ 7.29-7.25 (m, 2H), 7.19-7.15 (m, 3H), 3.53 (d, J=4.9 Hz, 1.3H), 3.45 (dd, J=5.5, 1.3 Hz, 0.7H), 2.84-2.75 (m, 1H), 1.65 (ddd, J=13.8, 8.9, 5.7 Hz, 0.35H), 1.61-1.52 (m, 1.3H), 1.47 (ddd, J=13.8, 7.7, 6.3 Hz, 0.35H), 1.39-1.26 (m, 3H), 1.23 (d, J=7.2 Hz, 1.05H), 1.22 (d, J=7.1 Hz, 1.95H), 0.85 (t, J=7.4 Hz, 1.05H), 0.82 (t, J=7.4 Hz, 1.95H);
$^{13}$CNMR (150 MHz, CDCl$_3$) δ 147.5 (2C), 128.4 (2C), 127.0, 126.9, 125.9 (2C), 65.3, 64.8, 39.6, 39.4 (2C), 39.0, 37.4, 37.3, 23.7, 23.1 (3C), 10.9, 10.7.

Production Example 2 Synthesis of Compounds 5 and 6

(1) 2-Phenyl-1-butanol (d) (1.00 g) was dissolved in dichloromethane (33 mL), subsequently iodobenzene diacetate (4.08 g) and TEMPO (208 mg) were added thereto and the solution was stirred at room temperature for 1.5 hours under nitrogen atmosphere. An aqueous solution of saturated sodium bicarbonate, an aqueous solution of sodium thiosulfate and hexane were added to the reaction solution and the hexane layer was dried under reduced pressure and subsequently purified by silica gel chromatography, thereby obtaining aldehyde (e) (640 mg).

Sodium hydride (purity 55%, 89.9 mg) was suspended in tetrahydrofuran (7 mL), triethyl 2-phosphonopropionate (0.56 mL) was added thereto and the solution was stirred for 30 minutes at room temperature under nitrogen atmosphere. A solution of the thus obtained aldehyde (e) (153 mg) dissolved in tetrahydrofuran (2 mL) was added to the reaction solution and further stirred for 14 hours. An aqueous solution of saturated ammonium chloride and hexane were added to the reaction solution and the hexane layer was dried under reduced pressure and subsequently purified by silica gel chromatography, thereby obtaining an α,β unsaturated ester (f) (E/Z=1:2, 160 mg).

Further, sodium hydride (purity 55%, 90.7 mg) was similarly suspended in tetrahydrofuran (7 mL), triethyl 2-phosphonobutyrate (0.62 mL) was added thereto and the solution was stirred for 30 minutes at room temperature under nitrogen atmosphere. A solution of aldehyde (e) (154 mg) dissolved in tetrahydrofuran (2 mL) was added to the reaction solution and further stirred for 14 hours. An aqueous solution of saturated ammonium chloride and hexane were added to the reaction solution and the hexane layer was dried under reduced pressure and subsequently purified by silica gel chromatography, thereby obtaining an α,β unsaturated ester (g) (E/Z=1:4, 152 mg).

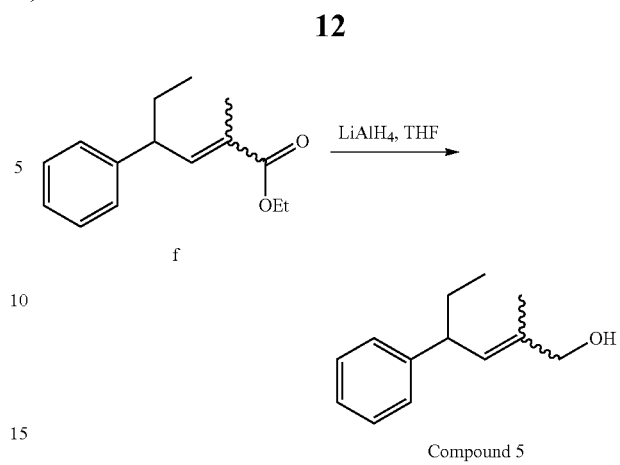

Compound 5

The NMR spectrum of Compound 5 is shown below.

$^1$HNMR (600 MHz, CDCl$_3$) δ 7.29-7.25 (m, 2H), 7.20-7.14 (m, 3H), 5.54 (d, J=9.6 Hz, 0.3H), 5.43 (d, J=9.8 Hz, 0.7H), 4.15 (s, 1.4H), 3.99 (s, 0.6H), 3.45-3.40 (m, 0.7H), 3.41-3.36 (m, 0.3H), 1.80 (d, J=1.3 Hz, 2.1H), 1.75-1.57 (m, 2H), 1.70 (d, J=1.2 Hz, 0.9H), 0.84 (t, J=7.4 Hz, 0.9H), 0.83 (d, J=7.4 Hz, 2.1H);

$^{13}$CNMR (150 MHz, CDCl$_3$) δ 145.7, 145.4, 134.6, 134.4, 132.5, 129.9, 128.5, 128.4, 127.3, 127.2, 126.0, 125.9, 68.8, 61.9, 45.7, 45.5, 30.1, 29.8, 21.5 (2C), 14.0, 12.2.

(3) Compound 5 (54.6 mg) obtained in (2) was dissolved in ethyl acetate (3 mL), Pd/C (10%, 27.3 mg) was added thereto under nitrogen atmosphere, subsequently the system was replaced with hydrogen gas and the solution was stirred at room temperature for 1 hours. The reaction solution was celite-filtered and the filtrate was dried under reduced pressure and purified by silica gel chromatography, thereby obtaining 2-methyl-4-phenyl-1-hexenol (dr=1:1, hereinafter Compound 6) (22.7 mg).

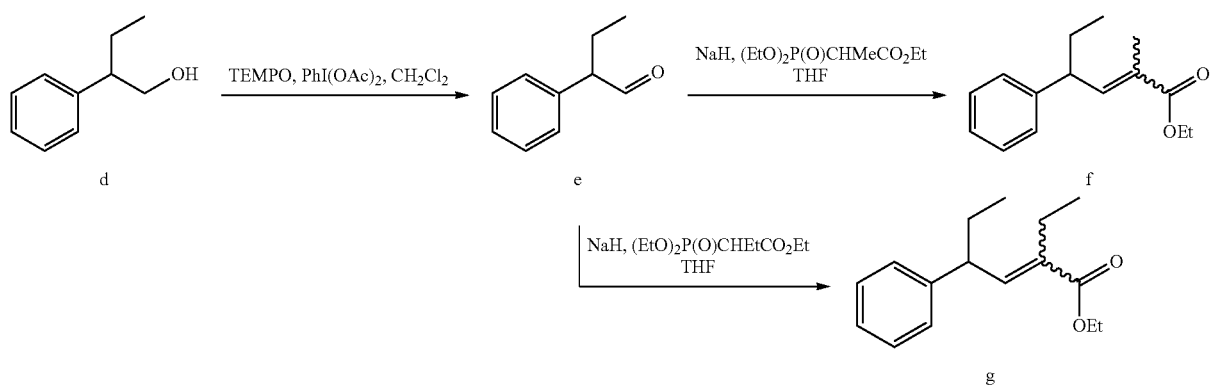

(2) LiAlH$_4$ (65.4 mg) was suspended in tetrahydrofuran (5 mL), a solution of the α,β unsaturated ester (f) (160 mg) obtained in (1) dissolved in tetrahydrofuran (1 mL) was added thereto and stirred at 0° C. for 30 minutes. Water (100 μL), a 15% sodium hydroxide aqueous solution (100 μL) and water (300 μL) were added in this order to the reaction solution and stirred for a day, followed by filtering the insoluble matters. The filtrate was dried under reduced pressure and purified by silica gel chromatography, thereby obtaining 2-methyl-4-phenyl-2-hexen-1-ol (E/Z=3:7, Compound 5) (99.6 mg).

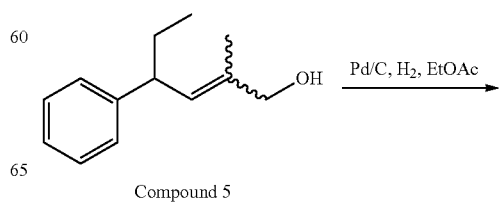

Compound 5

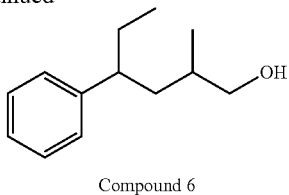

Compound 6

The NMR spectrum of Compound 6 is shown below.

$^1$HNMR (600 MHz, CDCl$_3$) δ 7.28-7.25 (m, 2H), 7.18-7.12 (m, 3H), 3.49 (dd, J=10.5, 4.9 Hz, 0.5H), 3.38 (dd, J=10.5, 6.4 Hz, 0.5H), 3.34 (dd, J=10.5, 5.8 Hz, 0.5H), 3.30 (dd, J=10.5, 6.2 Hz, 0.5H), 2.54-2.48 (m, 1H), 1.73-1.27 (m, 5H), 0.87 (d, J=6.4 Hz, 1.5H), 0.84 (d, J=6.8 Hz, 1.5H), 0.75 (t, J=7.3 Hz, 1.5H), 0.73 (t, J=7.3 Hz, 1.5H);

$^{13}$CNMR (150 MHz, CDCl$_3$) δ 145.8, 145.3, 128.2 (2C), 127.7, 127.6, 125.9 (2C), 68.8, 67.6, 45.1, 45.0, 40.1, 39.7, 33.3, 33.2, 30.8, 29.8, 17.5, 16.0, 12.2, 12.1.

Production Example 3 Synthesis of Compounds 7 and 8

LiAlH$_4$ (52.2 mg) was suspended in tetrahydrofuran (5 mL), subsequently a solution of the α,β unsaturated ester (g) (136 mg) obtained in Production Example 2 (1) dissolved in tetrahydrofuran (1 mL) was added thereto and the solution was stirred at 0° C. for 30 minutes. Water (80 μL), a 15% sodium hydroxide aqueous solution (80 μL) and water (240 μL) was added in this order to the reaction solution and stirred for a day, followed by filtering the insoluble matters. The filtrate was dried under reduced pressure and purified by silica gel chromatography, thereby obtaining 2-ethyl-4-phenyl-2-hexen-1-ol (E/Z=1:4) (84.6 mg). The obtained compound (a mixture) (20.0 mg) was purified by ODS-HPLC (Inertsil ODS-3, an aqueous solution of 50% acetonitrile/0.1% formic acid), thereby obtaining (E)-2-ethyl-4-phenyl-2-hexen-1-ol (Compound 7) (3.4 mg) and (Z)-2-ethyl-4-phenyl-2-hexen-1-ol (Compound 8) (13.6 mg).

The NMR spectrum of Compound 7 is shown below.

$^1$HNMR (600 MHz, CDCl$_3$) δ 7.28-7.25 (m, 2H), 7.20-7.14 (m, 3H), 5.51 (d, J=9.8 Hz, 1H), 4.04 (s, 2H), 3.39 (dt, J=9.8, 7.4 Hz, 1H), 2.16 (q, J=7.6 Hz, 2H), 1.76-1.68 (m, 1H), 1.67-1.59 (m, 1H), 0.97 (t, J=7.6 Hz, 3H), 0.84 (t, J=7.4 Hz, 3H);

$^{13}$CNMR (150 MHz, CDCl$_3$) δ 145.5, 140.3, 129.9, 128.4, 127.3, 125.9, 66.7, 45.4, 30.0, 21.3, 13.2, 12.3.

The NMR spectrum of Compound 8 is shown below.

$^1$HNMR (600 MHz, CDCl$_3$) δ 7.29-7.25 (m, 2H), 7.20-7.14 (m, 3H), 5.44 (d, J=9.8 Hz, 1H), 4.19 (d, J=11.9 Hz, 2H), 4.13 (d, J=11.9 Hz, 1H), 3.46 (m, 1H), 2.14 (m, 2H), 1.76-1.68 (m, 1H), 1.66-1.58 (m, 1H), 1.03 (t, J=7.5 Hz, 3H), 0.84 (t, J=7.4 Hz, 3H);

$^{13}$CNMR (150 MHz, CDCl$_3$) δ 145.8, 140.1, 131.3, 128.5, 127.2, 126.0, 60.7, 45.3, 30.3, 28.0, 12.8, 12.2.

Production Example 4 Synthesis of Compound 9

(1) 1-Phenyl-2-propanol (h) (428 mg) was dissolved in dichloromethane (16 mL), subsequently molecular sieves 4 A (400 mg), N-methylmorpholine (1.10 g) and tetrapropylammonium perruthenate (110 mg) were added thereto and the solution was stirred for 24 hours at room temperature under nitrogen atmosphere. The reaction solution was filtered using a silica gel short column, and the filtrate was dried under reduced pressure and subsequently purified by silica gel chromatography, thereby obtaining ketone (i) (102 mg).

Sodium hydride (purity 55%, 81.2 mg) was suspended in tetrahydrofuran (5 mL), triethyl 2-phosphonopropionate (0.48 mL) was added thereto and the solution was stirred for 30 minutes at room temperature under nitrogen atmosphere. A solution of the thus obtained ketone (i) (100 mg) dissolved in tetrahydrofuran (2 mL) was added to the reaction solution and further stirred for 22 hours. An aqueous solution of saturated ammonium chloride and hexane were added to the reaction solution and the hexane layer was dried under reduced pressure and subsequently purified by silica gel chromatography, thereby obtaining an α,β unsaturated ester (j) (E/Z=1:1, 97.6 mg).

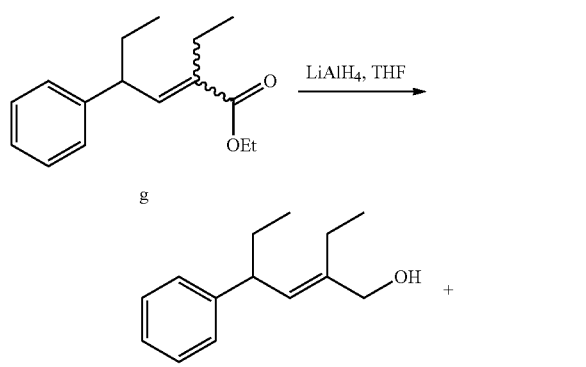

Compound 7

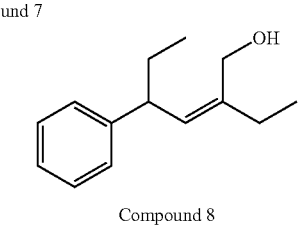

Compound 8

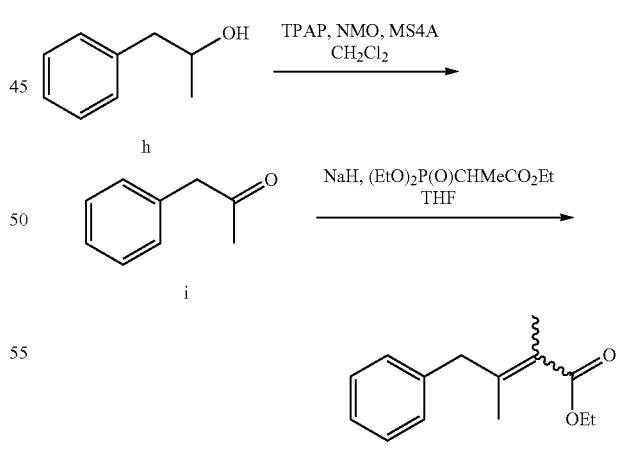

(2) LiAlH$_4$ (37.6 mg) was suspended in tetrahydrofuran (3 mL) and a solution of the α,β unsaturated ester (j) (86.5 mg) obtained in (1) dissolved in tetrahydrofuran (1 mL) was added thereto and stirred at 0° C. for 30 minutes. Water (50 μL), a 15% sodium hydroxide aqueous solution (50 μL) and water (150 μL) were added in this order to the reaction solution and stirred for a day, followed by filtering the insoluble matters. The filtrate was dried under reduced pressure and purified by silica gel chromatography, thereby obtaining allylalcohol (k) (E/Z=1:1) (49.4 mg).

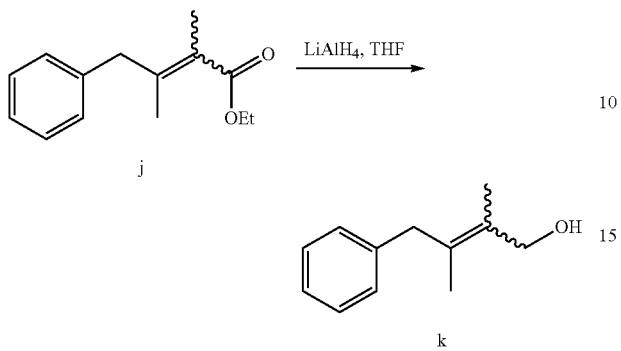

(3) Allylalcohol (30.0 mg) obtained in (2) was dissolved in ethyl acetate (3 mL), Pd/C (10%, 15.0 mg) was added thereto under nitrogen atmosphere, subsequently the system was replaced with hydrogen gas and the solution was stirred at room temperature for 1 hours. The reaction solution was celite-filtered and the filtrate was dried under reduced pressure and subsequently purified by silica gel chromatography, thereby obtaining 2,3-dimethyl-4-phenyl-1-butanol (dr=3:2, Compound 9) (17.4 mg).

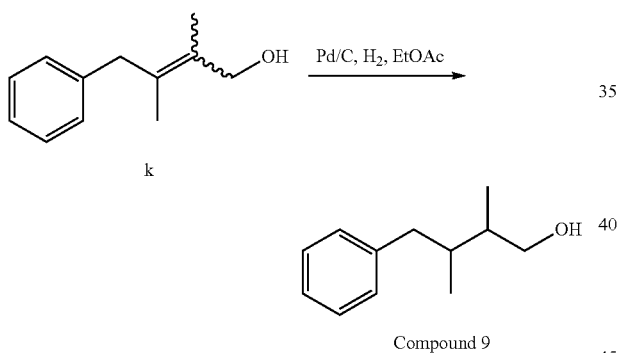

The NMR spectrum of Compound 9 is shown below.

$^1$HNMR (600 MHz, CDCl$_3$) δ 7.28-7.24 (m, 2H), 7.18-7.13 (m, 3H), 3.68 (dd, J=10.5, 5.8 Hz, 0.4H), 3.55-3.44 (m, 1.6H), 2.76 (dd, J=13.4, 4.8 Hz, 0.4H), 2.64 (dd, J=13.5, 6.8 Hz, 0.6H), 2.44 (dd, J=13.5, 8.4 Hz, 0.6H), 2.26 (dd, J=13.4, 9.9 Hz, 0.4H), 2.01-1.94 (m, 0.6H), 1.90-1.83 (m, 0.4H), 1.70-1.62 (m, 1H), 0.97 (d, J=7.0 Hz, 1.2H), 0.87 (d, J=6.9 Hz, 1.8H), 0.82 (d, J=7.0 Hz, 1.2H), 0.77 (d, J=6.9 Hz, 1.8H);

$^{13}$CNMR (150 MHz, CDCl$_3$) δ 141.7, 141.4, 129.1, 129.0, 128.2 (2C), 125.7 (2C), 66.7, 65.9, 41.4, 40.3, 39.4, 38.8, 36.9, 35.4, 16.6, 14.0, 13.7, 11.1.

Production Example 5 Synthesis of Compound 10

(1) 2-Phenylpropionaldehyde (a) (300 mg) was dissolved in tetrahydrofuran (10 mL) and subsequently ethyl 2-(triphenylphosphoranylidene)propionate (1.70 g) was added thereto and the solution was stirred for 24 hours at room temperature under nitrogen atmosphere. Water and hexane/ethyl acetate were added to the reaction solution and the organic layer was dried under reduced pressure and subsequently purified by silica gel chromatography, thereby obtaining (E)-α,β unsaturated ester (1) (261 mg).

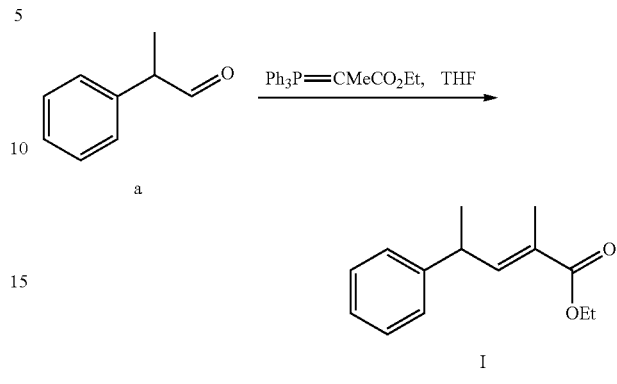

(2) LiAlH$_4$ (227 mg) was suspended in tetrahydrofuran (10 mL) and a solution of the (E)-α,β unsaturated ester (1) (261 mg) obtained in (1) dissolved in tetrahydrofuran (2 mL) was added thereto and stirred at 0° C. for 30 minutes. Water (200 μL), a 15% sodium hydroxide aqueous solution (200 μL) and water (600 μL) were added in this order to the reaction solution and stirred for a day, followed by filtering the insoluble matters. The filtrate was dried under reduced pressure and subsequently purified by silica gel chromatography, thereby obtaining (E)-2-methyl-4-phenyl-2-penten-1-ol (Compound 10) (115 mg).

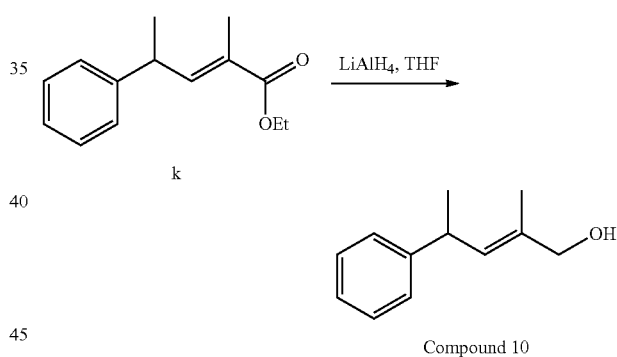

The NMR spectrum of Compound 10 is shown below.

$^1$HNMR (600 MHz, CDCl$_3$) δ 7.29-7.26 (m, 2H), 7.23-7.21 (m, 2H), 7.18-7.15 (m, 1H), 5.55 (dq, J=9.4, 1.3 Hz, 1H), 3.99 (s, 2H), 3.69 (dq, J=9.4, 6.9 Hz, 1H), 1.72 (d, J=1.3 Hz, 3H), 1.32 (d, J=6.9 Hz, 3H);

$^{13}$CNMR (150 MHz, CDCl$_3$) δ 146.4, 133.7, 131.2, 128.4, 126.9, 126.0, 68.7, 37.7, 22.1, 13.8.

Production Example 6 Synthesis of Compounds 11

LiAlH$_4$ (30.6 mg) was suspended in tetrahydrofuran (2 mL), 2-methyl-4-phenyl-1-butanoic acid (m) (47.9 mg) dissolved in tetrahydrofuran (0.5 mL) was added thereto and stirred at 0° C. for 30 minutes. Water (50 μL), a 15% sodium hydroxide aqueous solution (50 μL) and water (150 μL) were added in this order to the reaction solution and stirred for a day, followed by filtering the insoluble matters. The filtrate was dried under reduced pressure and subsequently purified by silica gel chromatography, thereby obtaining 2-methyl-4-phenyl-1-butanol (Compound 11) (16.5 mg).

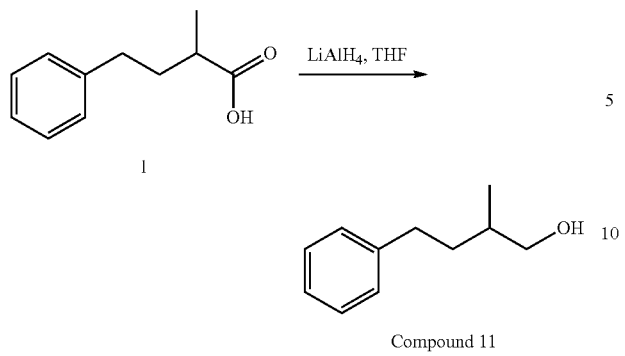

Compound 11

The NMR spectrum of Compound 11 is shown below.
¹HNMR (600 MHz, CDCl₃) δ7.28-7.25 (m, 2H), 7.19-7.14 (m, 3H), 3.51 (dd, J=10.5, 5.8 Hz, 1H), 3.45 (dd, J=10.5, 6.4 Hz, 1H), 2.69 (ddd, J=13.7, 10.4, 5.6 Hz, 1H), 2.58 (ddd, J=13.7, 10.2, 6.4 Hz, 1H), 1.78-1.71 (m, 1H), 1.69-1.61 (m, 1H), 1.46-1.39 (m, 1H), 0.97 (d, J=6.8 Hz, 3H);
¹³CNMR (150 MHz, CDCl₃) δ 142.6, 128.3 (2C), 125.7, 68.1, 35.3, 34.9, 33.2, 16.5.

Production Example 7 Synthesis of Compound 12

(1) Compound 1 (532 mg) was dissolved in dichloromethane (20 mL), subsequently iodobenzene diacetate (2.88 g) and TEMPO (93.2 mg) were added thereto and the solution was stirred at room temperature for 1.5 hours under nitrogen atmosphere. An aqueous solution of saturated sodium bicarbonate, an aqueous solution of sodium thiosulfate and ethyl acetate were added to the reaction solution and subsequently the ethyl acetate layer was dried under reduced pressure and purified by silica gel chromatography, thereby obtaining aldehyde (n) (361 mg).

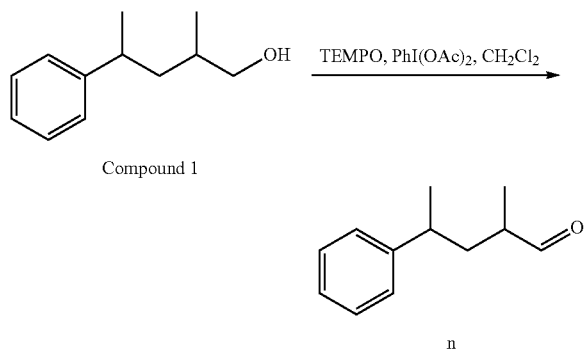

(2) The aldehyde (n) (31.1 mg) obtained in (1) was dissolved in tetrahydrofuran (2 mL), subsequently methyl magnesium bromide (3M in diethyl ether, 0.088 mL) was added thereto at 0° C. under nitrogen atmosphere and the solution was stirred at the same conditions for 30 minutes. An aqueous solution of saturated ammonium chloride and ethyl acetate were added to the reaction solution and the ethyl acetate layer was dried under reduced pressure and subsequently purified by silica gel chromatography, thereby obtaining 3-methyl-5-phenyl-2-hexanol (dr=3:2:2:2, Compound 12) (24.5 mg).

Compound 12

The NMR spectrum of Compound 12 is shown below.
¹HNMR (600 MHz, CDCl₃) δ 7.30-7.26 (m, 2H), 7.21-7.15 (m, 3H), 3.74 (qd, J=6.4, 4.0 Hz, 0.33H), 3.67 (qd, J=6.3, 5.2 Hz, 0.22H), 3.59 (qd, J=6.4, 4.2 Hz, 0.22H), 3.55 (qd, J=6.3, 5.0 Hz, 0.22H), 2.84-2.74 (m, 1H), 1.85-1.74 (m, 0.44H), 1.69-1.55 (m, 0.78H), 1.51-1.45 (m, 0.33H), 1.45-1.34 (m, 1H), 1.32-1.16 (m, 0.44H), 1.24 (d, J=7.0 Hz, 0.67H), 1.24 (d, J=6.9 Hz, 0.67H), 1.22 (d, J=6.9 Hz, 1H), 1.21 (d, J=7.0 Hz, 0.67H), 1.12-1.09 (m, 1.67H), 1.06 (d, J=6.4 Hz, 0.67H), 1.04 (d, J=6.3 Hz, 0.67H), 0.87-0.83 (m, 3H);
¹³CNMR (150 MHz, CDCl₃) δ 148.2, 148.1, 146.9 (2C), 128.4 (3C), 128.3, 127.1, 127.0, 126.9, 126.8, 125.9 (3C), 125.8, 72.0, 71.6 (2C), 70.9, 41.6, 41.4, 40.7, 40.6, 37.7, 37.4 (2C), 37.2 (3C), 37.1 (2C), 24.1, 24.0, 21.7, 21.4, 20.2, 19.7, 19.2, 18.9.

Production of Comparative Compounds (1) LiAlH₄ (30.0 mg) was suspended in tetrahydrofuran (2 mL), a solution of 4-phenyl-1-pentanoic acid (o) (46.9 mg) dissolved in tetrahydrofuran (0.5 mL) was added thereto and stirred at 0° C. for 30 minutes. Water (50 μL), a 15% sodium hydroxide aqueous solution (50 μL) and water (150 μl) were added in this order to the reaction solution and stirred for a day, followed by filtering the insoluble matters. The filtrate was dried under reduced pressure and subsequently purified by silica gel chromatography, thereby obtaining 4-phenyl-1-pentanol (Comparative Compound 1) (8.1 mg).

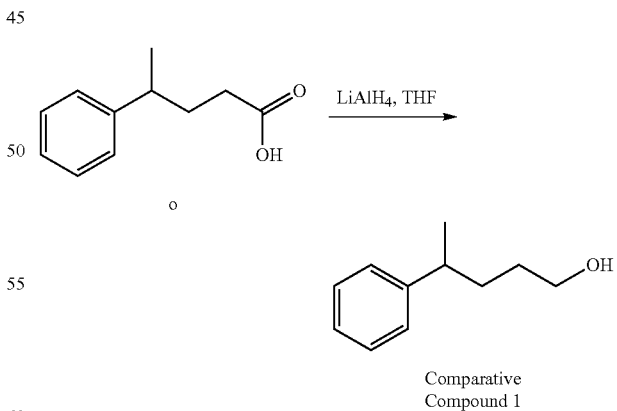

Comparative Compound 1

The NMR spectrum of Comparative Compound 1 is shown below.
¹HNMR (600 MHz, CDCl₃) δ 7.29-7.25 (m, 2H), 7.18-7.15 (m, 3H), 3.57 (t, J=6.6 Hz, 2H), 2.68 (qt, J=7.0, 7.0 Hz, 1H), 1.66-1.59 (m, 2H), 1.55-1.46 (m, 1H), 1.44-1.37 (m, 1H), 1.24 (d, J=7.0 Hz, 3H);

$^{13}$CNMR (150 MHz, CDCl$_3$) δ 147.3, 128.3, 126.9, 125.9, 63.0, 39.8, 34.4, 30.9, 22.4.

(2) For 4-phenyl-1-butanol (Comparative Compound 2), a commercial product (Tokyo Chemical Industry Co., Ltd.: P1275) was used.

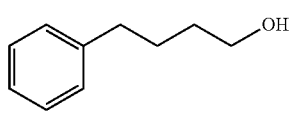

Comparative Compound 2

Example 1 The Effect of TRPA1 Inhibitor (1)

(1) Preparation of Human TRPA1 Stably Expressing Cell Line

The human TRPA1 gene of which the full length is inserted into pENTR223.1 was purchased from Open Biosystems. The TRPA1 gene was sub-cloned into an expression vector pcDNA3.2-V5/DEST (Invitrogen) and transfected into HEK293 cells using Lipofectamine 2000 (Invitrogen). The transfected cells were grown in DMEM medium containing G-418 (450 µg/ml; Promega KK) and thus selected. The HEK293 cells do not express endogenous TRPA1 and hence can be used as a control against the TRPA1-transfected cell line.

(2) Calcium Imaging

The activity of TRPA1 transfected into the HEK293 cell was measured using the fluorescent calcium imaging method. First, the cultured TRPA1 expressing cells were inoculated in a poly-D-lysine coated 96-well plate (BD Falcon) (30000 cells/well) and incubated at 37° C. overnight and subsequently the culture medium was removed therefrom, followed by adding Fluo4-AM (2 µg/ml; Dojin Chemical Co. Ltd) dissolved in a Ringer's solution to incubate the cells at 37° C. for 60 minutes. After that, the fluo4-AM solution was removed and a Ringer's solution was added to the well, and a fluorescent plate reader (FDSS3000; Hamamatsu Photonics K.K.) was set. A fluorescent image, excited at an excitation wavelength of 480 nm and a temperature inside the reader of 24° C., was detected using a CCD camera at a detection wavelength of 520 nm. The measurement was carried out every second for 4 minutes, and 15 seconds later from the start of measurement, a TRPA1 stimulant of AITC and a test material (2-methyl-4-phenyl-1-pentanol (Compound 1)) were added respectively at the final concentrations of 30 µM and 0.01% using an FDSS3000 built-in dispenser to evaluate the TRPA1 activities by the changes of fluorescence intensity thereafter. The TRPA1 activity is expressed as the fluorescence intensity ratio (Ratio; $F_{peak}/F_0$) calculated by dividing the peak of fluorescence intensity ($F_{peak}$) after the addition of stimulant by the fluorescence intensity ($F_0$) before the addition of stimulant. As a control, the same substance was added to HEK293 cells into which TRPA1 was not transfected and the fluorescence intensity ratio (Ratio$_{293}$) in this case was calculated to verify that the activity triggered by the stimulant was resulted from the TRPA1 activation.

(3) Evaluation of the Inhibitory Effect on TRPA1 Activation Caused by AITC

To evaluate the effect of Compound 1 on the TRPA1 activation caused by AITC, the inhibition (ratio for TRPA1 inhibition; %) of Compound 1 on TRPA1 activity when AITC (30 µl) and ethanol (0.01%; solvent control) were added was evaluated. The inhibitory effect on TRPA1 activity attained by mixing and adding AITC (stimulant) (30 µM) and Compound 1 (test material) (0.01%) was calculated in accordance with the following expression.

Ratio for TRPA1 inhibition (%)=(1−((Ratio obtained by the addition of stimulant+test material)−(Ratio$_{293}$ obtained by the addition of stimulant+test material))/((Ratio obtained by the addition of stimulant+ethanol)−(Ratio$_{293}$ obtained by the addition of stimulant+ethanol)))×100

(4) Inhibitory Effect on TRPA1 Activation Caused by AITC

Table 2 shows the effect (ratio for TRPA1 inhibition) of Compound 1 on the TRPA1 activation by 30 µM of AITC. It is verified that 2-methyl-4-phenyl-1-pentanol is a highly effective TRPA1 inhibitor compared with d-camphor, a known TRPA1 inhibitor.

TABLE 2

| Material Name | Ratio for TRPA1 inhibition (%) |
|---|---|
| 0.01% Compound 1 | 92.7 |
| 0.01% Camphor | 6.9 |
| 0.03% Camphor | 89.7 |

Example 2 The Effect of TRPA1 Inhibitor (2)

The inhibitory effect of 2-methyl-4-phenyl-1-pentanol (Compound 1) on TRPA1 activation was evaluated for the dose dependency. The effect of 1 to 100 µM of Compound 1 on the TRPA1 activation induced by 30 µM of AITC was measured (FIG. 1). As a result, the dose dependency was found in the inhibitory effect of 2-methyl-4-phenyl-1-pentanol on TRPA1 activation and the IC$_{50}$ value was 17.9 µM.

Example 3 The Effect of TRPA1 Inhibitor (3)

The inhibitory effect of 2-methyl-4-phenyl-1-pentanol (Compound 1) on the TRPA1 activation induced by TRPA1 stimulants other than AITC was evaluated.

As TRPA1 stimulants, cinnamaldehyde, 4-hydroxynonenal, allicin and l-menthol were prepared, and the effect of Compound 1 on the TRPA1 activation induced respectively by 20 µM (cinnamaldehyde), 30 µM (4-hydroxynonenal), 300 nM (allicin) and 200 µM (l-menthol) was studied. The results are shown in Table 3 and FIG. 2.

TABLE 3

| TRPA1 stimulant | Inhibitory ratio (%) |
|---|---|
| Allyl isothiocyanate (20 µM) | 96.6 |
| Cinnamaldehyde (20 µM) | 79.8 |
| 4-Hydroxynonenal (30 µM) | 72.1 |
| Allysine (0.3 µM) | 98.8 |
| Menthol (0.2 mM) | 100 |

As a result, the inhibitory effect of Compound 1 on the TRPA1 activation induced by any of cinnamaldehyde, 4-hydroxynonenal, allicin and l-menthol was verified.

Example 4 TRPA1 Activation Induced by Antiseptic and the Inhibitory Action Thereon To study the TRPA1 activation caused by a raw material used as an antiseptic or an antiseptic aid and the effect of 2-methyl-4-phenyl-1-pentanol (Compound 1) thereon, the TRPA1 activation caused by, as antiseptics, phenoxyethanol (20 to 30 mM), iodopropynyl butylcarbamate (IPBC) (0.03 to 0.1 mM) and triclosan (0.1 to 0.3 mM) and, as an antiseptic aid, benzyl alcohol (20 to 30 mM) were evaluated for the TRPA1 activation. Further, the ratio for TRPA1 inhibition of Compound 1 (0.1 to 0.5 mM) when stimulated by phenoxyethanol (20 mM), IPBC (0.03 mM), triclosan (0.1 mM) and benzyl alcohol (20 mM) were measured. The results are shown in FIG. 3.

FIG. 3 revealed that all of phenoxyethanol, IPBC, triclosan and benzyl alcohol activate TRPA1 in a dose dependent manner. Further, the inhibitory effect of Compound 1 was evaluated and the inhibitory effect on TRPA1 activation was confirmed (Table 4).

TABLE 4

|  |  | Ratio for TRPA1 inhibition (%) | | |
|---|---|---|---|---|
|  |  | Compound 1 | | Camphor |
| TRPA1 stimulant | (mM) | 0.1 mM | 0.5 mM | 0.5 mM |
| Phenoxyethanol | 20 | 78.76 | 85.24 | 13.96 |
| Benzyl alcohol | 20 | 48.86 | 84.35 | −0.89 |
| Triclosan | 0.1 | 84.47 | 95.57 | 27.45 |
| IPBC | 0.03 | 93.97 | n.d. | 32.40 |

Example 5 The Effect of 2-methyl-4-phenyl-1-pentanol (Compound 1) for Reduction of Sensory Irritation on Human Skin (1) Selection of Test Subjects To evaluate the skin sensory irritation, 22 women (age 20 to 59) having high sensitivity (1% lactic acid-sensitive, low current perception threshold and sensitive skin conscious with medical history of allergic disease) were selected as the subjects.

(2) Evaluation of Sensory Irritation Property to Antiseptic

After washing the face, the subjects entered a constant temperature-humidity room (room temperature 20° C., humidity about 50%) and were acclimated for 20 minutes, followed by applying 300 ill of distilled water heated to 37° C. in one side of the face from the cheek to the nose. 1, 2, 2.5, 5 and 8 minutes after the application, the degree (intensity) of unpleasant sensation (pain) reported in accordance with the following unpleasant sensation reference values was notated.

0.0; None or pleasant sensation
0.5; Slight discomfort barely detectable
1.0; Mild discomfort, detectable sensation but tolerable
1.5; Mild to moderate discomfort
2.0; Moderate discomfort, unpleasant feeling but tolerable
2.5; Moderate to severe discomfort
3.0; Severe discomfort, intense unpleasant feeling The distilled water was wiped off 8 minutes later, 300 μl of an antiseptic solution (0.2% methylparaben (MP)+0.35% phenoxyethanol (Phe) aqueous solution) was applied to the same part to notate the degrees of unpleasant sensation in the same manner. Subsequently, the antiseptic solution was wiped off and 300 μl of a test material solution (the preservative solution+0.05% Compound 1) was applied to the same part of the distilled water applied side to notate the degree of discomfort in the same manner. The maximum value of discomfort values is extracted and the test was carried out by the Willcoxon signed-rank test method. The results are shown in FIG. 4.

FIG. 4 revealed that the discomfort (pain) score was significantly increased by the antiseptic application compared with the distilled water application and that the discomfort (pain) was reduced by Compound 1.

Example 6 The Inhibitory Effect of 2-methyl-4-phenyl-1-pentanol (Compound 1) on Irritating Odor (1) Method Five evaluation-specialized panelists of ammonia stimulation (panelists who can distinctively perceive the stimulation from ammonia steam having a concentration of 150 to 200 ppm and also present the same score on repeated evaluations on the stimulation intensity) sniffed, for 1 minute, a test perfume (Compound 1) volatilized and saturated for 5 hours or more in a 100 ml glass bottle (temperature 25° C., humidity 45%), and for 10 minutes immediately after sniffing, the ammonia odor (irritating odor) was evaluated. Ammonia was volatilized and saturated by putting a cotton ball impregnated with a 28% ammonia water (20 μl) in a 50 ml syringe for 12 hours or more. The intensity of ammonia odor (irritating odor) was evaluated using a 7-stage scale (0 to 6). Comparative evaluation was carried out without sniffing the test perfume.

(2) Evaluation scale 0; No irritating odor, 1; very faint, 2: faint, 3; easily noticeable, 4; strong, 5; very strong, 6; extremely strong (3) Results Table 5 shows the average values (round off to the nearest integer) of ammonia odor (irritating odor) scores.

TABLE 5

|  | Immediately after inhalation | 1 minute later | 2 minutes later | 5 minutes later | 6 minutes later | 10 minutes later |
|---|---|---|---|---|---|---|
| Example | 1 | 2 | 2 | 2 | 3 | 3 |
| Comparative Example | 3 | 3 | 3 | 3 | 3 | 3 |

Table 5 revealed that the ammonia odor (irritating odor) was reduced by the inhalation of the test perfume and the effect was further maintained for 5 minutes after the inhalation.

Example 7 Evaluation for the Inhibitory Effect on TRPA1 Activation

In the same manner as in Example 1, the inhibitory effects on TRPA1 activation (ratio for TRPA1 inhibition) of the following Compounds of the present invention, Comparative Compounds (100 μM each) and d-camphor (100 μM, 500 μM) to the TRPA1 activation induced by 5.0 and 10 μM of AITC were evaluated (Table 6).

TABLE 6

|  | Ratio for TRPA1 inhibition (%) | |
|---|---|---|
| Compound | 10 μM AITC | 5.0 μM AITC |
| Compound 1 | 80.8 | 100 |
| Compound 2 | 73.8 | 99.4 |
| Compound 3 | 101.6 | 103.7 |
| Compound 4 | 101.1 | 70.5 |
| Compound 5 | 27.6 | 83.4 |
| Compound 6 | 9.7 | 18.7 |
| Compound 7 | 101.7 | 103.3 |

TABLE 6-continued

| | Ratio for TRPA1 inhibition (%) | |
|---|---|---|
| Compound | 10 μM AITC | 5.0 μM AITC |
| Compound 8 | 101.0 | 101.9 |
| Compound 9 | 51.7 | 89.5 |
| Compound 10 | 31.8 | 92.9 |
| Compound 11 | 3.9 | 19.5 |
| Compound 12 | 27.1 | 54.9 |
| Comparative Compound 1 | 0.0 | N.D. |
| Comparative Compound 2 | 0.8 | 0.0 |
| d-Camphor (100 μM) | 0.0 | 1.8 |
| d-Camphor (500 μM) | 15.1 | 27.8 |

Table 6 revealed that Compounds of the present invention are highly effective materials for inhibition of TRPA1 activity compared with d-camphor, a known TRPA1 inhibitor.

Example 8 The Effect of TRPA1 Inhibitor (2)

The inhibitory effects of 2-methyl-4-phenyl-1-pentanol (Compound 1), (E)-2-ethyl-4-phenyl-2-penten-1-ol (Compound 2), (Z)-2-ethyl-4-phenyl-2-penten-1-ol (Compound 3), 2-ethyl-4-phenyl-1-pentanol (Compound 4), (E)-2-ethyl-4-phenyl-2-hexen-1-ol (Compound 7), (Z)-2-ethyl-4-phenyl-2-hexen-1-ol (Compound 8) and (E)-2-methyl-4-phenyl-2-penten-1-ol (Compound 10) on TRPA1 activation were studied for the dose dependency.

The effect of each Compound on the TRPA1 activation induced by 5.0 μM of AITC was measured (FIGS. 5(A), 5(B) and 5(C)) and the $IC_{50}$ value of each Compound is shown in Table 7. As a result, the dose dependency was found in the inhibitory effect on TRPA1 activation of each Compound.

TABLE 7

| Compound | 50% inhibitory concentration (μM) |
|---|---|
| Compound 1 | 7.7 |
| Compound 2 | 5.8 |
| Compound 3 | 10.6 |
| Compound 4 | 3.1 |
| Compound 7 | 3.4 |
| Compound 8 | 2.0 |
| Compound 10 | 32.5 |

What is claimed is:

1. A method for inhibiting TRPA1 activity comprising contacting a subject with
   (a) a TRPA1 activity-inhibiting amount of a compound represented by the following formula (1) and
   (b) an amount of a TRPA1 stimulant that causes irritation in the absence of the compound, wherein the compound represented by formula (1) is:

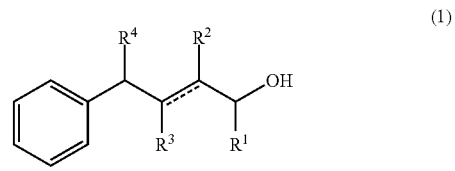

(1)

wherein $R^1$ and $R^3$ each independently represent a hydrogen atom or an alkyl group having 1 to 3 carbon atoms, $R^2$ represents an alkyl group having 1 to 6 carbon atoms, $R^4$ represents a hydrogen atom, a methyl group or an ethyl group, and a double line composed of a dotted line and a solid line represents a single bond or a double bond, and inhibiting the TRPA1 stimulant's induction of TRPA1 activity, wherein the TRPA1 stimulant is an antiseptic, allyl isothiocyanate (AITC), ammonia, bradykinin, cinnamaldehyde, 4-hydroxynonenal, allicin, acrolein, menthol, methyl salicylate, eugenol, parabens, phenoxyethanol, iodopropynyl butylcarbamate, triclosan or benzyl alcohol.

2. The method according to claim 1, wherein $R^1$ and $R^3$ are both hydrogen atoms or either one of them is an alkyl group having 1 to 3 carbon atoms.

3. The method according to claim 1, wherein $R^1$ and $R^3$ are both hydrogen atoms or either one of them is a methyl group.

4. The method according to claim 1, wherein $R^2$ is an alkyl group having 1 to 3 carbon atoms.

5. The method according to claim 1, wherein $R^2$ is a methyl group or an ethyl group.

6. The method according to claim 1, wherein $R^1$ is a hydrogen atom or a methyl group, $R^2$ is a methyl group or an ethyl group, $R^3$ is a hydrogen atom and $R^4$ is a methyl group or an ethyl group.

7. The method according to claim 1, wherein $R^1$ and $R^3$ are both hydrogen atoms, $R^2$ and $R^4$ are both methyl groups and a double line composed of a dotted line and a solid line is a single bond.

8. The method of claim 1, wherein the compound represented by formula (1) is in a composition together with the TRPA1 stimulant.

9. The method of claim 1, wherein the compound represented by formula (1) and the TRPA1 stimulant are in separate compositions.

10. The method of claim 1, wherein the stimulant is ammonia.

11. The method of claim 1, wherein the TRPA1 activity that is to be inhibited is activity induced by a volatile odor, the presence of which is perceived by inhalation, and the administering comprises inhaling the compound represented by formula (1) by the subject.

* * * * *